United States Patent [19]

Frobel et al.

[11] Patent Number: 4,927,810

[45] Date of Patent: May 22, 1990

[54] EFOMYCIN G AND IT'S USE AS YIELD PROMOTER IN ANIMALS

[75] Inventors: Klaus Frobel, Wuppertal; Hartwig Müller, Velbert; Erwin Bischoff, Wuppertal; Olga Salcher, Wuppertal; Anno de Jong, Wuppertal; Friedrich Berschauer, Wuppertal; Martin Scheer, Wuppertal-Elberfeld, all of Fed. Rep. of Germany

[73] Assignee: Bayer Aktiengesellschaft, Leverkusen, Fed. Rep. of Germany

[21] Appl. No.: 22,915

[22] Filed: Mar. 6, 1987

[30] Foreign Application Priority Data

Mar. 12, 1986 [DE] Fed. Rep. of Germany ....... 3608175

[51] Int. Cl.$^5$ .......... A61K 31/71; C07H 7/06
[52] U.S. Cl. ...... 514/23; 514/32; 536/1.1; 536/7.1; 536/16.8; 435/72; 435/74; 435/886
[58] Field of Search ......... 536/7.1, 16.8, 1.1; 514/32, 23

[56] References Cited

FOREIGN PATENT DOCUMENTS 0197360 10/1986 European Pat. Off. ............ 536/7.1

OTHER PUBLICATIONS

Manipulating Rumen Fermentation (William Chalupa, 'Journal of Animal Science', vol. 46, No. 3, 1977, pp. 585–599.

*Primary Examiner*—Johnnie R. Brown
*Assistant Examiner*—Elli Peselev
*Attorney, Agent, or Firm*—Sprung Horn Kramer & Woods

[57] ABSTRACT

An animal growth promoter, efomycin G, is obtained by culturing Streptomycetes strain BS 1261. Efomycin G has the following properties:

(a) The empirical formula: $C_{53}H_{86}O_{18}$
(b) The mass spectrum (fast atom bombardment) Molecular weight+Na$^+$: 1033
(c) The $^1$H-nuclear magnetic resonance spectrum, stated in parts per million, shown in FIG. 1.
(d) The $^{13}$C-nuclear magnetic resonance spectrum, stated in parts per million shown in FIG. 2, with chemical shifts of the CC-NMR signals as follows:

| | | | | |
|---|---|---|---|---|
| 170.0 | 77.9 | 65.9 | 32.9 | 7.0 |
| 145.4 | 73.4 | 48.5 | 19.4 | |
| 144.7 | 71.2 | 43.6 | 19.1 | |
| 131.9 | 70.6 | 41.9 | 16.8 | |
| 121.1 | 70.1 | 41.1 | 16.7 | |
| 99.6 | 69.9 | 38.8 | 15.1 | |
| 99.5 | 66.9 | 38.5 | 13.4 | |
| 93.6 | 66.5 | 36.2 | 9.0 | |
| 93.3 | 66.4 | 33.0 | 8.9 | |

(ppm values are relative to tetramethylsilane at 0 ppm)

(ppm values are relative to tetramethylsilane at 0 ppm)
(e) A UV absorption maximum at 251–254 nm in methanolic solution
(f) The structure according to FIG. 3.

4 Claims, 3 Drawing Sheets

EFOMYCIN G AND IT'S USE AS YIELD PROMOTER IN ANIMALS

The invention relates to efomycin G, its preparation and its use as a yield promoter in animals.

1. Efomycin G with the chemical and physical properties mentioned below has been found:
   1. The empirical formula: $C_{53}H_{86}O_{18}$
   2. The mass spectrum (fast atom bombardment) Molecular weight $+Na^+$: 1033
   3. The $^1H$-nuclear magnetic resonance spectrum, stated in parts per million, according to FIG. 1.
   This was recorded in an AM 300 from Bruker at MHz in a solution of efomycin G in deuterated chloroform with tetramethylsilane as the internal standard.
   4. The $^{13}C$-nuclear magnetic resonance spectrum, stated in parts per million, according to FIG. 2.
   This was recorded in an AM 300 from Bruker at 75.48 MHz on a solution of efomycin g in deuterated chloroform and deuterated methanol with tetramethylsilane as the internal standard.
   The chemical shifts of the $^{13}C$-NMR signals of efomycin G according to FIG. 2 are, in detail:

| | | | | |
|---|---|---|---|---|
| 170.0 | 77.9 | 65.9 | 32.9 | 7.0 |
| 145.4 | 73.4 | 48.5 | 19.4 | |
| 144.7 | 71.2 | 43.6 | 19.1 | |
| 131.9 | 70.6 | 41.9 | 16.8 | |
| 121.1 | 70.1 | 41.1 | 16.7 | |
| 99.6 | 69.9 | 38.8 | 15.1 | |
| 99.5 | 66.9 | 38.5 | 13.4 | |
| 93.6 | 66.5 | 36.2 | 9.0 | |
| 93.3 | 66.4 | 33.0 | 8.9 | |

5. The UV absorption maximum at 251-254 nm in methanolic solution.
   6. The structure according to FIG. 3.

2. It has been found that the efomycin G according to the invention is obtained when suitable microorganisms of the Streptomycetaceae family are cultured under aerobic conditions in a nutrient medium containing assimilable carbon and nitrogen sources and mineral salts, and the resulting mixture of the efomycins is isolated by customary methods and separated.

With knowledge of the properties of efomycin G, it is possible, with the aid of the customary chromatographic, spectroscopic and/or biological detection methods, to identify suitable microorganism strains which produce efomycin G.

The Streptomyces strain BS 1261—and its mutants and variants—can be used in particular for carrying out the process.

This strain belongs to the family of Streptomycetaceae, the genus Streptomyces from the grey series of Streptomycetes (Cinereus group).

The strain BS 1261 was deposited in the Deutsche Sammlung fur Mikroorganismen (DSM) (German collection of microorganisms), Grisebachstrasse 8, 3400 Göttingen, Federal Republic of Germany under number DSM 3200 on 16.01.1985.

Taxonomic description of the strain BS 1261 (DSM 3200)

The taxonomic description of the strain BS 1261 was drawn up in accordance with *Bergey's Manual of Determinative Bacteriology* 8th, (1974) and *International Journal of Systematic Bacteriology* 16, 313–340 (1966) and The Prokaryotes 2., 2028–2020 (1981).

1. Morphology

Good sporulation was to be observed on ISP media No. 2, 3, 4, 5 and 7 to 9. Predominantly substrate mycelium was formed on ISP medium No. 9 with ribose as the C source and from ISP medium No. 1 to 6.

| Air mycelium (ISP medium No. 3, 28° C., 7 days): | |
|---|---|
| Color | grey (Cinereus type) |
| Spore chains: | Retinaculum-Apertum type |
| Spores: | Square to rectangular, 1.4–1.8 $\sigma$m long and 1.3–1.6 $\mu$m wide smooth (electron microscopy). |
| Substrate mycelium: | |
| Color | brown |

2. Physiology information

The optimum temperature is 28° C. (on ISP medium No. 2, 5 days). The strain does not grow at 4° or 45° C. No melanine is formed. Growth is inhibited by the antibiotics erythromycin (10 $\sigma$g), sulphafurazole (100 $\mu$g), streptomycin (10 $\sigma$g) and novobiocin (5 $\mu$g) (ISP medium No. 2, 28° C., 2 days).

The utilization of C sources was tested on basal agar (ISP medium No. 9) in accordance with the method of Int. Syst. Bact. 16, 313–340 (1966). For negative control the growth on basal agar without a C source was compared. The following results are thereby obtained:

TABLE

| Utilization of C sources by strain BS 1261 | |
|---|---|
| C source (10 g/l) | Growth* |
| Control (no C source) | − |
| D-Glucose | + |
| L-Arabinose | + |
| L-Rhamnose | + |
| D-Fructose | + |
| L-Galactose | + |
| Raffinose | + |
| D-mannitol | + |
| meso-Inositol | + |
| Salicin | + |
| Sucrose | + |
| Ribose | + |
| Mannose | + |
| Maltose | + |
| Mellibiose | + |
| Cellulose | − |
| Acetate | − |

*+ = growth,
− = no growth.

3. Particularly suitable medium for growth and sporulation

ISP 3 (oatmeal agar)

20 g of oatmeal are suspended in a 1000 ml of deionized $H_2O$ and the suspension is boiled for 20 minutes. It is then filtered, 1 ml of trace element solution for ISP 3 and 18 g of agar are added, the pH value is brought to 7.2 and the mixture is autoclaved at 121° C. for 15–20 minutes.

| Trace element solution for ISP 3 | |
|---|---|
| $FeSO_4.7\ H_2O$ | 0.1 g |
| $MnCl_2.4\ H_2O$ | 0.1 g |
| $ZnSO_4.7\ H_2O$ | 0.1 g |

| -continued |   |
| --- | --- |
| Trace element solution for ISP 3 |   |
| Deionized H$_2$O | 100 ml |

For further media, see Int. J. Syst. Bact. 16, 313–340 (1966).

The strain BS 1261, isolated from a soil sample from New Zealand, can be classified in the grey series of Streptomycetes (Cinereus group) on the basis of the morphological data.

Taxonomic designation: Streptomyces sp.

Efomycin G is produced according to the invention by fermentation of suitable microorganisms, such as the Streptomycetes strain BS 1261 or mutants or variants thereof.

The fermentation process according to the invention can be carried out with the aid of solid, semi-solid or liquid nutrient media. Aqueous liquid nutrient media are preferably used.

The nutrient media are inoculated by generally customary methods, for example via slant tubes or flask cultures.

Culture is effected under aerobic conditions and can be carried out in accordance with the generally customary methods, such as using shaken cultures and submerged cultures. Culture is preferably effected by the aerobic submerge process in aerated fermenters, for example in the customary submerge fermentation tanks. It is possible to carry out the fermentation continuously or discontinuously. The discontinuous procedure is preferably used.

Culture is effected in nutrient media which are known to be used for culture of microorganisms of the order Actinomycetales. The nutrient medium must contain one or more assimilable carbon sources and nitrogen sources as well as mineral salts, it being possible for these products to be present in the form of defined individual constituents or in the form of complex mixtures, such as are given, in particular, by biological products of various origins. Possible carbon sources are all the customary carbon sources. Examples which may be mentioned are carbohydrates, in particular polysaccharides, such as starch or dextrins, disaccharides, such as maltose or lactose, monosaccharides, such as glucose of xylose, alcohols, such as mannitol or glycerol, and naturally occurring mixtures, such as malt extract, molasses or whey powder. Possible nitrogen sources are all the customary organic and inorganic nitrogen sources. Examples which may be mentioned are proteins, protein hydrolysates, amino acids, nucleoside bases, such as cytosine or uracil, and soy bean flour, cottonseed flour, linseed flour, pea flour, soluble and insoluble vegetable proteins, corn steep liquor, yeast extract, peptones and meat extract, and nitrogen-containing salts, such as, for example, ammonium salts and nitrates. The mineral salts which the nutrient medium should contain supply, for example, the following ions:

$Mg^{++}$, $Na^+$, $K^+$, $Ca^{++}$, $NH_4^+$, $Cl^-$, $SO_4^{--}$, $PO_4^{---}$ and ions of the customary trace elements, such as Cu, Fe, Mn, Mo, Zn, CO and Ni. If the carbon or nitrogen sources or the water used do not contain a sufficient quantity of these salts or trace elements, it is advantageous to supplement the nutrient medium accordingly. The composition of the nutrient media can vary within wide limits. The nature and composition of the nutrient media in general depend on what constituents are in each case particularly advantageously available. In general, the nutrient solutions contain preferably about 0.5 to 8%, in particular 0.6 to 6%, of carbon sources, preferably about 0.5 to 4%, in particular 0.5 to 2%, of nitrogen sources, and preferably about 0.001 to 0.5%, in particular 0.003 to 3%, of mineral salts.

In carrying out the process, it may be advantageous to use only relatively low concentrations of the soluble nutrient solution constituents at the start of the culture and then to feed these constituents to the culture batch in fractions in the form of sterile, relatively concentrated solutions by more frequent additions in the course of the first 3 days of culture.

The pH value of the growing cultures should preferably be kept between about 5 and about 10, in particular between 6.5 and 8.0. Too sharp a drop in the pH into acid ranges can be avoided by addition of an organic or inorganic base, preferably CaCO$_3$. As is customary in fermentation technology, automatic pH control can also be carried out, in which sterile organic or inorganic acids, for example H$_2$SO$_4$, or sterile alkalis, for example NaOH, are injected into the culture solution at intervals of time.

It is advantageous to ensure that the microorganisms are brought into sufficient contact with oxygen and the nutrients. This can be effected by the generally customary methods, such as shaking and stirring.

The culture temperature can be between about 24° C. and about 34° C., preferably between 26° C. and 32° C., and is particularly preferably about 28° C. The duration of the culture can be varied greatly, the composition of the nutrient medium and the culture temperature, for example, playing a role. The particular optimum conditions can easily be determined by any expert in the microbiological field.

It has been found that the amount of compounds according to the invention which become concentrated in the culture broth in general achieve their maximum about 1 to 10, preferably about 4 to 7, days after the start of culture. The desired end product of the fermentation can be determined with the aid of investigations by thin layer chromatography and high pressure liquid chromatography or biological test methods.

As is generally customary in microbiological processes, foreign infections of the culture media should be avoided. The customary measures are taken for this, such as sterilization of the nutrient media, culture vessels and the air required for the aeration. Both steam sterilization and dry sterilization, for example, can be used to sterilize the devices, it being possible for the temperatures to be preferably 100° to 140° C., in particulr 120° to 130° C.

If an undesirable amount of foam is formed during the culture, the customary chemical foam suppressants, for example liquid fats and oils, such as oil-in-water emulsions, paraffins, higher alcohols, such as octadecanol, silicone oils or polyoxyethylene or polyoxypropylene compounds (for example in amounts of up to about 1%), can be added. Foam can also be suppressed or eliminated with the aid of the customary mechanical devices (which use, for example, centrifugal forces).

The compound according to the invention can be isolated from the culture medium by generally customary physico-chemical methods. Isolation can be effected, for example, by the customary extraction processes, precipitation processes and/or chromatography processes. The substances isolated can also be finely purified with the aid of the methods mentioned. For many cases, however, fine purification is not necessary, since any small amounts of impurities present do not adversely influence the activity of the compounds. In all the isolation and purification operations it should be ensured that the pH values are in the neutral range. The pH values are preferably kept between 7 and 8. Inorganic and organic bases, such as alkali metal bases, for example NaOH or KOH, or organic amines, such as triethylamine; or inorganic acids, such as, for example, HCl, and organic acids, such as, for example, acetic acid, can be used to establish the pH value.

The customary physico-chemical methods, for example measurement of a characteristic band in the spectrum or of the $R_f$-values, determination of the antibacterial activity and the like, can be used to discover the fractions in which the compound according to the invention is present in the highest concentration or purity in the abovementioned isolation and purification methods. These physico-chemical methods can also be used to discover suitable microorganisms for the production of efomycin G in routine processes.

The isolation and purification of the compound according to the invention can be carried out as follows, for example in the case where a liquid aqueous nutrient medium is used:

Since efomycin G is to be found both in the culture supernatant and in the mycelium, it can be isolated from the fermentation batch with the aid of customary extraction processes, precipitation processes and/or chromatography processes and if appropriate purified. The chromatography can be carried out in the form of column chromatography. High pressure liquid chromatography (HPLC) can also be employed with good success. The customary inorganic or organic adsorbents can be employed as the adsorbents, such as, for example, silica gel, magnesium silicate, active charcoal, cellulose, cellulose derivatives, synthetic resins, such as polyamides, for example acetylated polyamide, dextrangels or modified dextrangels. The most diverse solvents or solvent mixture in which the compounds according to the invention are soluble, can be used as the mobile phase. Ethyl acetate, chloroform and methanol or their mixtures (for example mixtures of chloroform and methanol or of ethyl acetate and chloroform) are preferably employed.

Chromatography processes, for example non-specific adsorption onto adsorbents such as silica gel, or on the other hand gel diffusion chromatography, are preferably used to isolate the compounds according to the invention. These processes are known from the purification of naturally occurring substances which have a poor water-solubility.

The compound according to the invention can be obtained from these solutions by customary methods, for example evaporation of the solvent, freeze-drying and the like.

In a preferred embodiment, the mycelium is separated off from the culture broth, preferably by centrifugation, and extracted several times, preferably twice, with a water-miscible solvent. Solvents which can be used are $(C_1-C_4)$-alkyl alcohols and $C_{1-4}$-ketones, particularly preferably acetone. The aqueous-organic solution is concentrated in vacuo, for example to about 1/20th of the volume of the culture broth, and freeze-dried.

This crude product is suspended in water and the efomycin G is extracted with a water-immiscible solvent, such as, for example, chlorohydrocarbons, such as chloroform, esters of acetic acid or ketones. Efomycin G can be isolated from this extract by customary chromatographic methods, preferably chromatography on silica gel.

Efomycin G can also be extracted from the culture filtrate by extraction with a water-immiscible solvent, such as, for example, ethyl acetate, methylene chloride or chloroform.

It can also be bonded to non-specific adsorber resins based on polystyrene (for example Amberlite XAD from Roehm u. Haas on Lewatit OC 1031 from Bayer). Desorption is carried out by fractionation using mixtures of water and organic solvents, in particular water/methanol. The active fractions determined by a test against *Staphylococcus aureus* 1756 are concentrated under reduced pressure at 30°-35° C. until the organic solvent has been removed completely, and the residue is suspended in about 1/100 of the volume of the culture filtrate and the suspension is freeze-dried.

The lyophilizate is suspended in water again and is preferably extracted with ethyl acetate or other water-immiscible solvents. Efomycin G is obtained from the extract by customary chromatographic methods, preferably chromatography on silica gel.

The novel material described in the accompanying drawings wherein, as described above:

Figure 1:
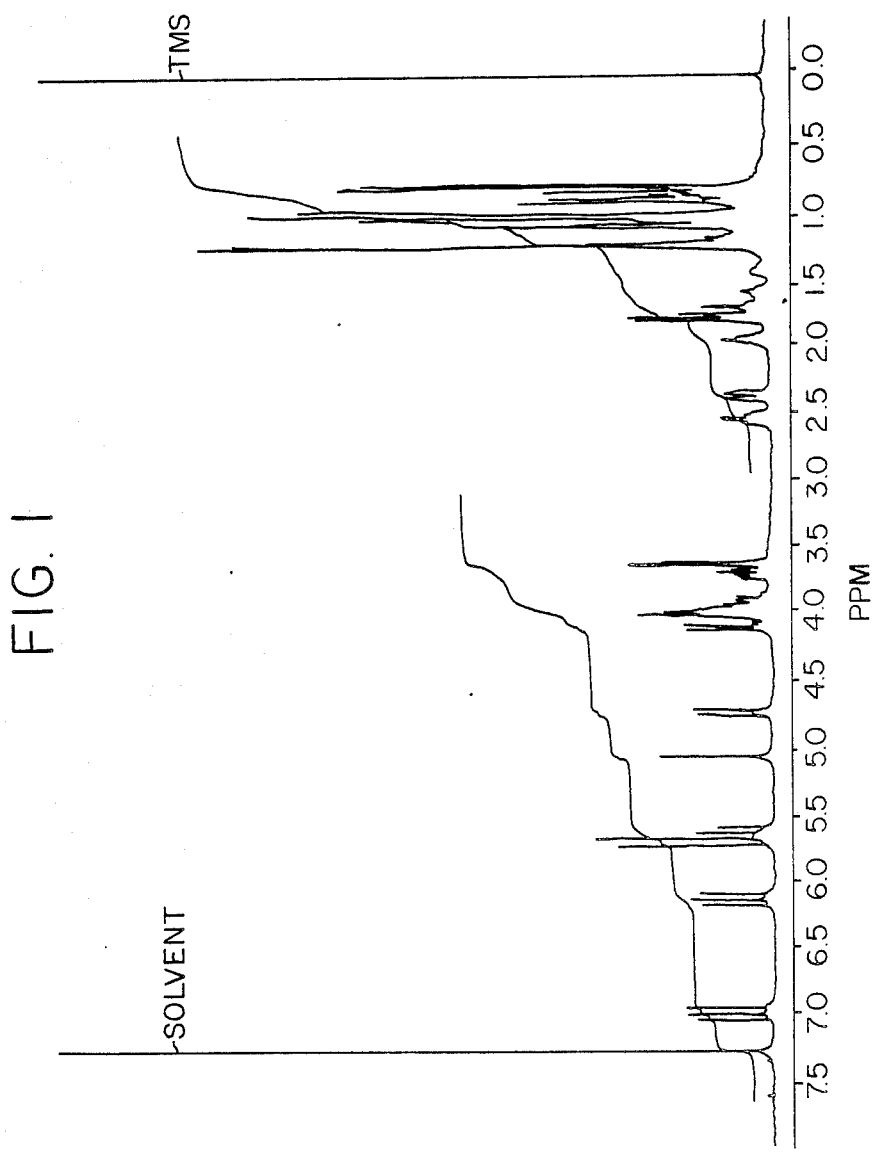
FIG. 1 is its $^1$H-nuclear magnetic resonance spectrum.

The compound according to the invention shows a good antibacterial action, above all against Gram-positive germs. Their suitability for preventing and curing dysentery in pigs and ketosis in dairy cattle should be mentioned in particular.

The active compound is used as a yield promoter in animals for promoting and accelerating growth and milk and wool production and for improving feed utilization and meat quality and for shifting the meat/fat ratio in favor of meat. The active compound is preferably in livestock animals. Ruminants such as cattle, sheep and goats are the major livestock animals.

The active compound is employed during all yield phases of the animals, independently of the sex of the animals. The active compound is preferably employed during the intensive yield phase. The intensive growth and yield phase lasts from one month to 10 years, depending on the animal species.

The amount of active compound administered to the animals to achieve the desired effect can be varied widely because of the advantageous properties of the active compound. It is preferably about 0.001 to 500 mg/kg, in particular 0.01 to 5 mg/kg of body weight per day. The appropriate amount of the active compound and the appropriate duration of the administration depend, in particular, on the species, age, sex, yield phase, state of health and nature of housing and feeding of the animals and can easily be determined by any expert.

The active compound is administered to the animals by the customary methods. The nature of the administration depends, in particular, on the species, behavior and state of health of the animals.

The active compound can be administered a single time. However, the active compound can also be administered temporarily or continuously throughout the entire or during part of the yield phase.

In the case of continuous administration, the active compound can be used once or several times daily at regular or irregular intervals.

Administration is effected orally in formulations suitable for this or in the pure form.

The active compound can be present in the formulations by itself or as a mixture with other yield-promoting active compounds, mineral feedstuffs, trace element compounds, vitamins, non-protein compounds, dyestuffs, antioxidants, aroma substances, emulsifiers, flow auxiliaries, preservatives and pressing auxiliaries.

Other yield-promoting active compounds are: for example, antibiotics, such as tylosin, virginiamycin and monensin. Mineral feedstuffs are, for example, dicalcium phosphate, magnesium oxide and sodium chloride.

Trace element compounds are, for example, iron fumarate, sodium iodide, cobalt chloride, copper sulphate and zinc oxide.

Vitamins are, for example, vitamin A, vitamin $D_3$, vitamin E, B vitamins and vitamin C.

Non-protein compounds are, for example, biuret and urea.

Dyestuffs are, for example, carotinoids, such as citranaxanthine, zeaxanthine and capsanthine.

Antioxidants are, for example, ethoxyquin and butyl-hydroxy-toluene.

Aroma substances are, for example, vanillin.

Emulsifiers are, for example, esters of lactic acid and lecithin.

Flow auxiliaries are, for example, sodium stearate and calcium stearate.

Preservatives are, for example, citric acid and propionic acid.

Pellet binders are, for example, ligninsulphonates and cellulose ethers.

The active compounds can also be administered together with the feed and/or the drinking water.

The feed includes individual foodstuffs of vegetable origin, such as hay, beet and cereal by-products, individual feedstuffs of animal origin, such as meat, fats, milk products, bonemeal and fish products, individual feedstuffs such as vitamins, proteins, amino acid, for example DL-methionine, and salts, such as lime and sodium chloride. The feed also includes supplementary, prepared and compound feedstuffs. These contain individual feedstuffs in a composition which ensure balanced nutrition in respect of energy and protein supply and supply with vitamins, mineral salts and trace elements.

The concentration of the active compound of the feed is usually about 0.01–500 ppm, preferably 0.1–50 ppm.

The active compound can be added to the feed as such or in the form of premixes or feed concentrates.

An example of the composition of a cattle feed containing the active compound according to the invention:

69.95% of crushed cereal meal feed, 10% of ground corn cobs, 8% of soy bean meal, 5% of alfalfa meal, 5% of molasses, 0.6% of urea, 0.5% of calcium phosphate, 0.5% of calcium carbonate, 0.3% of sodium chloride and 0.15% premix. The premix contains 70.000 IU vitamin A, 7.000 IU vitamin D3, 100 mg vitamin E, 50 mg manganese, 30 mg zinc and 0.06 mg cobalt. Efomycin G should be added to the premix in the amounts required.

It is not absolutely necessary to use purified and isolated efomycin G. It is also possible for the mixture obtained during its preparation, or even the culture broth obtained or the mycelium, to be employed without purification, if appropriate after drying. For many purposes it is also sufficient to employ crude forms of the active compound according to the invention and its mixtures without prior fine purification.

The preparation and biological action of the new compound according to the invention can be illustrated by the following examples:

EXAMPLE 1

Preparation of the inoculum

Cells of Streptomyces sp. BS 1261 (DSM 3200) were transferred from a slant tube into a 1000 ml conical flask each containing 150 ml of the following sterile nutrient solution:

| CASO ® from Merck, Darmstadt, with the composition: | |
|---|---|
| Casein peptone | 15 g |
| Soy flour peptone | 5 g |
| D-Glucose | 2.5 g |
| NaCl | 5 g |
| Water | to 1000 ml |

The flasks were incubated at 28° C. on a rotating shaking machine at 250 Rpm for 3 days. 2 flasks of the resulting culture were combined and were used as the inoculum for a 30 l fermenter containing 20 l of the above sterile nutrient solution, to which 20 ml of SAG 5693 (Union Carbide) had been added.

Fermentation was carried out at 28° C. at an aeration rate of 10 l/minute (0.5 VVM) of air under a blanketing pressure of 0.5 bar. The speed of rotation of the blade stirrer was 300 revolutions per minute. After 48 hours, the culture thus obtained was used as the inoculum for the tank fermentation.

EXAMPLE 2

Tank fermentation 20 liters of the inoculum prepared according to Example 1 were used to inoculate a 300 l vessel containing 200 l of sterile nutrient medium of the following composition:

| Skimmed milk powder | 10 g |
|---|---|
| Yeast autolyzate | 1.5 g |
| Dextrin | 40 g |
| D-Glucose | 5 g |
| SAG 5693 (Union Carbide) | 1 ml |
| Water | to 1000 ml |

After sterilization, the pH value of the medium was 6.6. The fermentation was carried out at 28° C. with a speed of rotation of the blade stirrer of 100 revolutions per minute and an aeration rate of 100 l/minute (0.5 VVM) of air under a blanketing pressure of 1.0 bar, until, after 3–5 days, efomycin G was to be detected.

Example 3

The culture broth obtained according to Example 2 from a 200 liter fermentation is separated at pH 7–7.5 and at 200–250 l/hour in a Westfalia separator. The mycelium is stirred with twice the volume of acetone at room temperature for 30 minutes and centrifuged. The residue is stirred again with twice the volume of acetone and centrifuged. The combined centrifugates are concentrated at a bath temperature of 40° C. under reduced pressure. 10 liter of water are added to the concentrate and the mixture is extracted three times with 10 liter of methylene chloride each time. The combined organic phases were dried over sodium sulphate, filtered and concentrated to 3 liter at a maximum bath temperature of 40° C. under reduced pressure. The concentrate was allowed to run in to about 30 liter of light petrol, with stirring. The precipitate was filtered off and dried at 40° C. in vacuo. Yield: 61 g of a yellowish powder.

EXAMPLE 4

Efomycin G was isolated from the crude product obtained according to Example 3 by prepared liquid chromatography.

Parameters

Mobile phase
  A: 5 mM citric acid:acetonitrile=6:4
  B: 5 mM citric acid:acetonitrile=4:6
Gradient: after 3 minutes, isocratic running with mobile phase A:B=4:1, linear gradient in 1 of A:B=4:1 to A:B=1:9.
Flow rate: 20 ml/minute
Detection: UV 254 nm
Column: 21.6×250 mm
Stationary phase: Zorbax ® C8 8 μm (DuPont)

About 30 mg of the crude product obtained according to Example 3, dissolved in 2 ml of tetrahydrofuran/water=2/1 in each case, were employed per separation. The column eluate was collected in fractions and subjected to analytical high pressure liquid chromatography in accordance with the following parameters.
Mobile phase A:
  5 mM citric acid
  0.1M $NaClO_4$
Mobile phase B: Acetonitrile
Gradient: Linear, 52–75% of B in 18 minutes
Flow rate: 1.5 ml/minute
Detection: UV 254 nm
Stationary phase: Nucleosil ® 10C18
Column: 4.6×250 ml Fractions which contained pure efomycin G were combined and were concentrated to ⅓ of the initial volume at a bath temperature of 40° C. under reduced pressure. The efomycin G obtained as a colorless precipitate was filtered off and dried at 40° C. under a high vacuum. Yield: 5 mg of efomycin G; purity according to HPLC: more than 85%.

EXAMPLE A:

Ruminal fluid was removed through a rumen fistula from a wether which received 650 g of coarsely ground sheep compound feed and 250 g of dried green cobs. The compound feed was administered by an automatic feeder in 12 equal portions at intervals of 2 hours and the cobs were administered in 2 equal portions at 08.30 and 16.15 hours. The rum/nal fluid was subjected to the following treatment immediately after being obtained: 2.5 ml of the rumenal inoculant were introduced into a test tube which was gassed with carbon dioxide, had a volume of 13 ml and moreover contained the following additives: 100 mg of finely ground sheep compound feed, 7.5 ml of buffer solution and 0.5 ml of a 5% aqueous ethanol solution with or without efomycin G.

The composition of the buffer solution, which was saturated with carbon dioxide before the start of the experiment, was as follows:

| | | |
|---|---|---|
| $Na_2HPO_4$ | 4.61 | g per liter of water |
| $NaHCO_3$ | 12.25 | g per liter of water |
| NaCl | 0.59 | g per liter of water |
| KCl | 0.71 | g per liter of water |
| $MgCl_2$ | 0.32 | g per liter of water |
| $CaCl_2$ | 0.13 | g per liter of water |

Each test tube was closed with a Bunsen stopper and incubated at 39° C. The batches were shaken manually after 2, 4, 6 and 8 hours. After incubation for 24 hours, 1.0 ml of the fermentation liquid was removed from the batches and pipetted into an Eppendorf vessel containing 0.2 ml of 10% strength phosphoric acid (containing $5.7 \times 10^{31}$ 6 μmol of 2-methylvaleric acid). The samples were centrifuged at 11,000 g and the volatile fatty acid concentrations in the supernatant were determined by gas chromatography.

The ratio of acetic acid to propionic acid was determined in each experiment. The value obtained with negative controls was set at 100 and the deviations in relation to this were stated. The more propionic acid formed, the lower the ratio of acetic acid to propionic acid and the smaller the ratio figure in comparison with the control (low ratio figure=reduced acetic acid/propionic acid ratio=improved feed utilization).

The concentrations of the total fatty acids in comparison with the control (=100) are additionally stated for each experiment.

TABLE

| Amount (μg/batch) | Acetic acid/ propionic acid ratio | Total fatty acids |
|---|---|---|
| Control | 100 | 100 |
| 250 | 64.3 | 101.5 |
| 500 | 58.8 | 103.8 |

Figure 2:
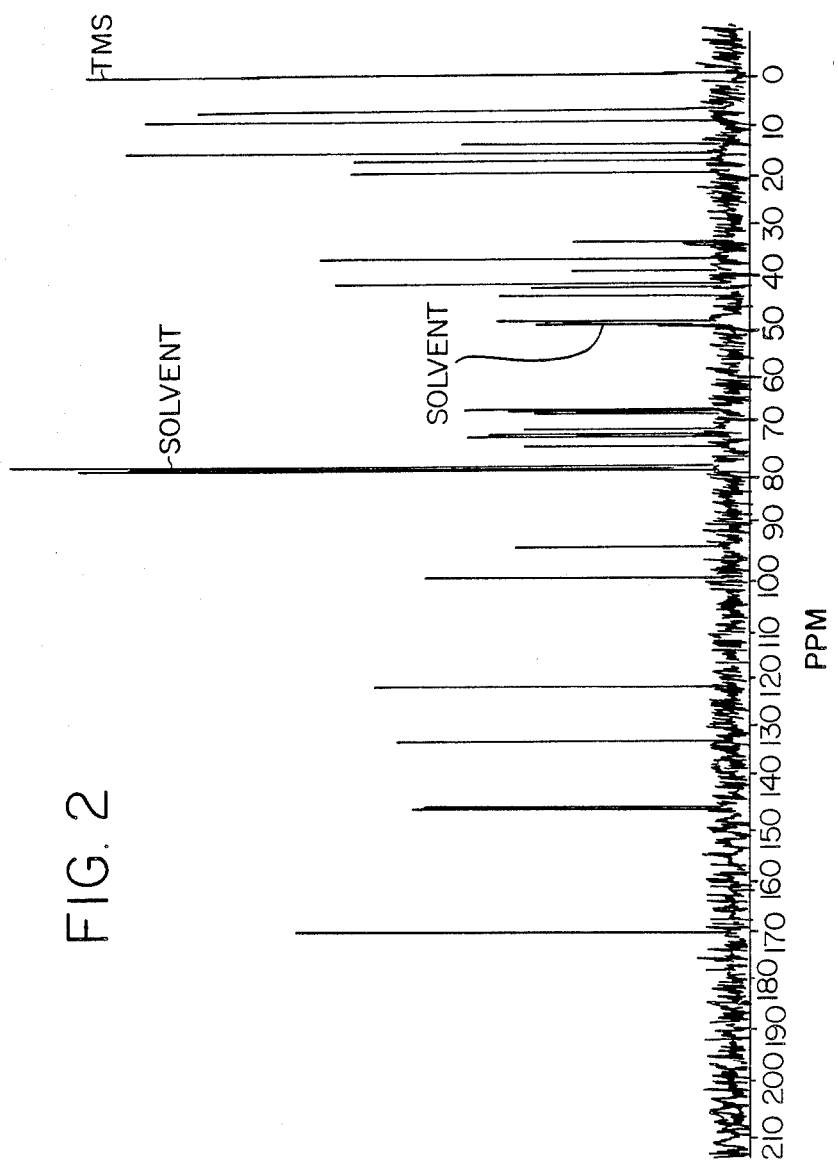
FIG. 2 is its $^{13}$C-nuclear magnetic resonance spectrum.
Figure 3:
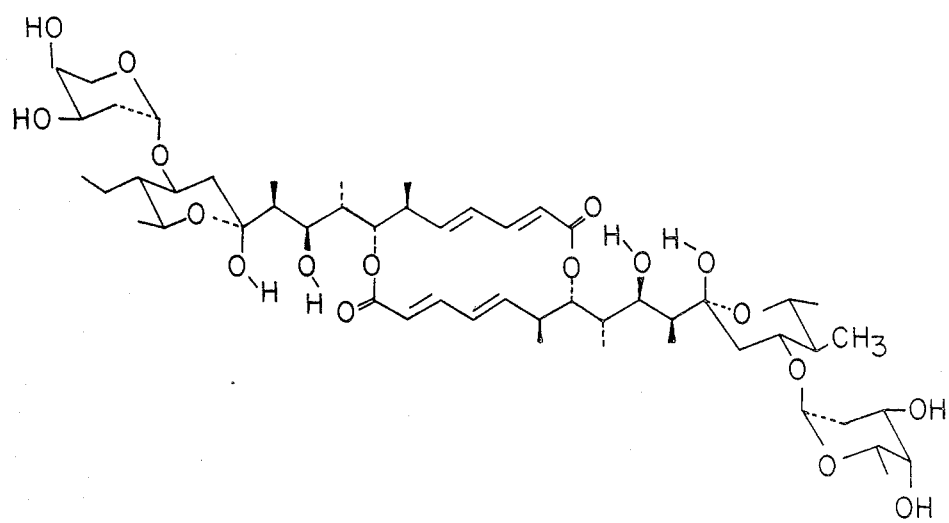
FIG. 3 is its structure.

We claim:
1. Efomycin G having the following properties:
  (a) The empirical formula: $C_{53}H_{86}O_{18}$
  (b) The mass spectrum (fast atom bombardment) Molecular weight $+Na^+$: 1033
  (c) The $^1H$-nuclear magnetic resonance spectrum, stated in parts per million, shown in FIG. 1.
  (d) The $^{13}C$-nuclear magnetic resonance spectrum, stated in parts per million shown in FIG. 2, with chemical shifts of the CC-NMR signals as follows:

| | | | | |
|---|---|---|---|---|
| 170.0 | 77.9 | 65.9 | 32.9 | 7.0 |
| 145.4 | 73.4 | 48.5 | 19.4 | |
| 144.7 | 71.2 | 43.6 | 19.1 | |
| 131.9 | 70.6 | 41.9 | 16.8 | |
| 121.1 | 70.1 | 41.1 | 16.7 | |
| 99.6 | 69.9 | 38.8 | 15.1 | |
| 99.5 | 66.9 | 38.5 | 13.4 | |
| 93.6 | 66.5 | 36.2 | 9.0 | |
| 93.3 | 66.4 | 33.0 | 8.9 | |

(ppm values are relative to tetramethylsilane at 0 ppm)

(e) A UV absorption maximum at 251–254 nm in methanolic solution.
  (f) Having the following structure:

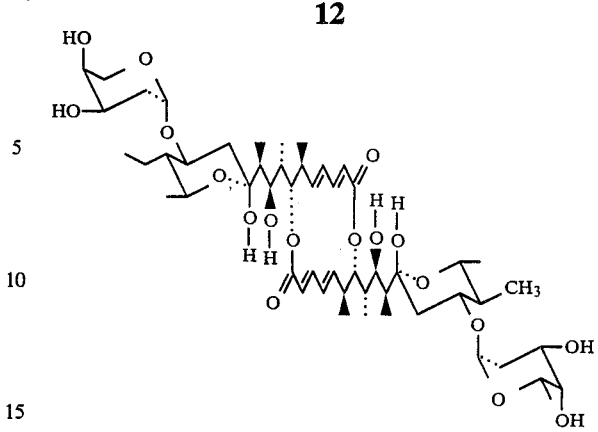
2. An animal growth promoting composition comprising an animal growth promoting effective amount of efomycin G and an edible carrier.
3. A composition according to claim 2, wherein the carrier is an animal feed base.
4. A method of promoting the growth of animals which comprises supplying to such animals an animal growth promoting effective amount of efomycin G.
* * * * *